(12) United States Patent
Sharpin (10) Patent No.: US 8,642,323 B2
(45) Date of Patent: Feb. 4, 2014

(54) CONTAINER FOR TESTING FOR MICRO-ORGANISMS

(75) Inventor: Rosemary Katherine Cameron Sharpin, Auckland (NZ)

(73) Assignee: Zyzeba Testing Limited, Auckland (NZ)

( * ) Notice: Subject to any disclaimer, the term of this patent is extended or adjusted under 35 U.S.C. 154(b) by 0 days.

(21) Appl. No.: 13/351,637

(22) Filed: Jan. 17, 2012

(65) Prior Publication Data

US 2012/0115216 A1 May 10, 2012

Related U.S. Application Data (62) Division of application No. 11/922,785, filed as application No. PCT/NZ2005/000139 on Jun. 23, 2005.

(30) Foreign Application Priority Data

Jun. 23, 2004 (NZ) ......................................... 533706

(51) Int. Cl.
*G01N 21/00* (2006.01)
*C12M 1/34* (2006.01)
*C12M 3/00* (2006.01)
*G01N 33/00* (2006.01)

(52) U.S. Cl.
USPC .................. 435/288.7; 422/82.05; 435/287.1; 435/288.6; 436/110

(58) Field of Classification Search
USPC ......... 435/288.7, 283.1–309.4; 436/110, 810; 422/82.05
See application file for complete search history.

(56) References Cited

U.S. PATENT DOCUMENTS

| | | | |
|---|---|---|---|
| 3,504,376 A * | 3/1970 | Reid et al. ..................... 436/165 |
| 3,715,189 A * | 2/1973 | Nighohossian et al. ...... 422/413 |
| 4,551,766 A | 11/1985 | Mosier et al. |
| 4,925,789 A | 5/1990 | Edberg |
| 5,003,611 A | 3/1991 | Miyake et al. |
| 5,164,301 A | 11/1992 | Thompson et al. |
| 5,284,772 A | 2/1994 | Oxley |
| 5,292,644 A | 3/1994 | Berg |
| 5,364,766 A | 11/1994 | Mach et al. |

(Continued)

FOREIGN PATENT DOCUMENTS

| | | |
|---|---|---|
| CA | 2176895 | 11/1996 |
| CA | 2199445 | 9/1997 |

(Continued)

OTHER PUBLICATIONS

International Search Report for International Application No. PCT/NZ2005/000139 dated Oct. 6, 2005.

(Continued)

*Primary Examiner* — Nathan Bowers
*Assistant Examiner* — Lydia Edwards
(74) *Attorney, Agent, or Firm* — Young & Thompson (57) ABSTRACT

A multi-compartment resealable container for testing for the presence of micro-organisms is provided with or adapted to receive a sample in a first substantially rigid transparent compartment, a growth medium in a second compartment, and a sanitizer in a third compartment, the compartments being separated by foil seals, the second and third compartments have an associated plunger which when depressed causes serrated cutters to puncture the foil seal and allow the contents to be added to the liquid containing or comprising the sample.

14 Claims, 8 Drawing Sheets

(56) References Cited

U.S. PATENT DOCUMENTS

| | | | |
|---|---|---|---|
| 5,393,662 | A | 2/1995 | Roth et al. |
| 5,411,867 | A | 5/1995 | Chang et al. |
| 5,429,933 | A | 7/1995 | Edberg |
| 5,496,518 | A | 3/1996 | Arai et al. |
| 5,501,959 | A | 3/1996 | Lancaster et al. |
| 5,518,892 | A | 5/1996 | Naqui et al. |
| 5,528,363 | A | 6/1996 | Fachinger et al. |
| 5,605,812 | A | 2/1997 | Zomer |
| 5,610,029 | A | 3/1997 | Ehrenfeld et al. |
| 5,620,865 | A | 4/1997 | Chen et al. |
| 5,620,895 | A | 4/1997 | Naqui et al. |
| 5,690,825 | A | 11/1997 | Parton |
| 5,700,655 | A | 12/1997 | Croteau et al. |
| 5,728,542 | A | 3/1998 | Charm et al. |
| 5,753,456 | A | 5/1998 | Naqui et al. |
| 5,780,259 | A | 7/1998 | Edberg |
| 5,817,475 | A | 10/1998 | Gibbs et al. |
| 5,827,675 | A | 10/1998 | Skiffington et al. |
| 5,965,453 | A | 10/1999 | Skiffington et al. |
| 5,985,594 | A | 11/1999 | Croteau et al. |
| 6,055,050 | A | 4/2000 | Skiffington |
| 6,287,797 | B1 | 9/2001 | Croteau et al. |
| 6,329,166 | B1 | 12/2001 | Edberg |
| 6,372,485 | B1 | 4/2002 | Clark et al. |
| 6,387,650 | B1 | 5/2002 | Townsend et al. |
| 6,472,167 | B1 | 10/2002 | Townsend et al. |
| 6,509,168 | B2 | 1/2003 | Croteau et al. |
| 6,597,450 | B1 | 7/2003 | Andrews et al. |
| 6,653,096 | B1 | 11/2003 | Christensen et al. |
| 6,730,496 | B2 | 5/2004 | Edberg |
| 6,783,950 | B2 | 8/2004 | Edberg |
| 6,849,422 | B1 | 2/2005 | Wiles et al. |
| 7,229,783 | B2 | 6/2007 | Saul et al. |
| 7,781,185 | B2 | 8/2010 | Goldman et al. |
| 2003/0027206 | A1 | 2/2003 | Ammann et al. |
| 2003/0032171 | A1* | 2/2003 | Gemmell et al. ......... 435/286.2 |

FOREIGN PATENT DOCUMENTS

| | | |
|---|---|---|
| EP | 0301699 | 2/1989 |
| EP | 1358459 | 11/2003 |
| FR | 2831182 | 4/2003 |
| JP | 9-159671 | 6/1997 |
| JP | 10-150976 | 6/1998 |
| NZ | 504061 | 1/2003 |
| NZ | 539210 | 9/2006 |
| NZ | 543476 | 11/2007 |
| WO | 90/02816 | 3/1990 |
| WO | 95/23026 | 8/1995 |
| WO | 95/33069 | 12/1995 |
| WO | WO9838104 | 9/1998 |
| WO | 01/69329 | 9/2001 |
| WO | 02/10708 | 2/2002 |
| WO | WO 2004/009756 | 1/2004 |
| WO | 2004/060766 | 7/2004 |
| WO | 2006/001716 | 1/2006 |
| WO | 2006/123946 | 11/2006 |

OTHER PUBLICATIONS

Supplementary European Search Report for EP 05 75 7540 dated Aug. 8, 2009.
ArTecPro. ArtecPro offering the Firefly and PocketSwab cleaning and restoration. Retrieved from archives of Mar. 6, 2005, from http://www.artecpro.com/index.htm.
ArTecPro. ArtecPro. Firefly ATP bioluminescence test for monitoring hygiene. Retrieved from archives of Mar. 6, 2005, from http://www.artecpro.com/firefly.htm.
ArTecPro. PocketSwab—the fastest ATP sanitation test of its kind. Retrieved from archives of Mar. 6, 2005, from http://www.artecpro.com/pocketswab/htm.
Bacteria Water Test. Retrieved Oct. 24, 2006 from http://www.bacteriawatertest.com/.
Charm Sciences Inc. Setting trends in Food Safety Diagnostics. Retrieved Oct. 23, 2006 from http://www.charm.com/.
Charm Sciences Inc. (2005). VERIcleen: Surface Hygiene Indicator.
Charm Sciences, Inc. (2006) FireFly 2—Hands on Approach to Hygiene Monitoring.
Charm Sciences, Inc. (2005). PocketSwab Plus—Now with Room Temperature Stability.
Charm Sciences, Inc. (2010) PocketSwab Plus—The Most Trusted Name in ATP Monitoring.
Charm Sciences, Inc. Pocket Swab Plus. Retrieved from archives of Feb. 19, 2006, from http://www.charm.com/personal_care.html.
Colifast. Products. Retrieved Nov. 13, 2006, from http://www.colifast.no/products2.htm.
Hygiena. News & Products Updates. Retrieved Jun. 9, 2011 from http://www.hygiena.net/index.html.
Idexx. Colilert—18 Water Testing Product Information. Retrieved Jun. 9, 2011 from http://www.idexx.com/view/xhtml/en_us/water/colilert-18.jsf.
Idexx. Enterolert-E Water Testing Product Information. Retrieved Jun. 9, 2011 from http://www.idexx.com/view/xhtml/en_us/water/enterolert-e.jsf.
Idexx. Quanti-Tray and Quanti-Tray/2000 Water Testing Product Information. Retrieved Jun. 9, 2011 from http://www.idexx.com/view/xhtml/en_us/water/quanti-tray/jsf.
MicroBio Corporation. Products. SensiMedia; Biomatic 20; Biomatic VDCS; Biomatic DMCS. Retrieved Oct. 24, 2006, from http://www.microbio.co.jp/Eng%20top.html.
Millipore Corporation. Millipore Products Catalogue—Samplers and Swab Test Kits. Retrieved Nov. 9, 2006 from http:// www. millipore.com/catalogue.nsf/docs/c6065.
Weber F., Weber Scientific, Inc. (2004). 69-5 SpotCheck: Non-instrument color hygiene test for on-the-spot cleaning validation. Retrieved Jul. 18, 2011, from http://ift.confex.com/ift/2004/techprogram/paper_26481.htlm.
University of Guelph, Dairy Science and Technology, Dye Reduction Tests: Methylene Blue and Resazurin, Retrieved Nov. 9, 2006 from http://www.foodsci.uoguelph.ca/dairyedu/resazurin.html.
European Official Action—05 757 540.9-2402—Sep. 26, 2012.

* cited by examiner

CONTAINER FOR TESTING FOR MICRO-ORGANISMS

TECHNICAL FIELD OF THE INVENTION

The present invention relates to improvements in and relating to the detection of microorganisms, and in particular to containers adapted to grow the micro-organisms for use in test apparatus of the type described and claimed in our co-pending U.S. application Ser. No. 11/922,785.

BACKGROUND ART KNOWN TO THE APPLICANT

It is known to measure the levels of micro-organisms in fluids such as drinking water by placing a sample of the fluid in a test cell with a dye or indicator such as Resazurin or methylene blue with optionally a nutrient medium and incubating the sample at a set temperature for a minimum time. A change in dye or indicator colour indicates the presence of micro-organisms as the growth reduces or otherwise reacts with the indicator chemical. It is also known to add suppressants to the sample to suppress the growth of other micro-organisms than that being tested for.

Typically the colour change is monitored by eye and the incubation process takes from 14 to 48 hours. Some micro-organism strains have a relatively high temperature sensitivity compared to others and the temperature may need to be maintained very close to a specific temperature in order to promote the relative growth of the species required to be detected. Thus, for instance, in some media, if it is desired to culture for the presence or absence of e. coli the required temperature of incubation may be 45° C., while if all coliform micro-organisms are being monitored the temperature is best set at 37° C.

The colour change is therefore a value judgement by eye, and may take considerable incubation time before it can be done.

These dye reduction tests are not considered to be reliable indicators of the type of microorganism or the quantity present. They provide a rough guide to indicate the presence or absence of micro-organisms.

There have been many attempts to develop tests to identify the micro-organism species or to determine the extent of contamination. Most such tests require samples to be couriered quickly (preferably in a chilled state) to a laboratory, where the samples are cultured for 24 to 48 hours (typically on agar plates) and the resulting cultures examined by microscope to determine the amount and type of micro-organisms present. Typical turn around times for such tests is 3 to 5 days, which is far too long to provide adequate warning of contamination in waterways or on beaches. Resulting in the closure of beaches long after the contamination has passed. The time delays in completing and reporting such tests for foodstuffs especially for shellfish, means that either the batches have to be recalled after dispatch or held in store for 5 days until clear test results have been received. Similarly lengthy bacteriological testing of poultry and of dairy products, among others, has enormous economic consequences. There is clearly a need for a far more rapid yet accurate testing system for the presence and type of micro-organisms so that any contamination can be dealt with promptly and the source of the contamination can be determined so that remedial action can be taken. This is especially so in food processing plants, but applies also to marine farms.

While instrumental optical measurement of the medium colour is known the instruments for doing this are normally laboratory level instruments and are largely unsuitable for use in the field and are generally not suitable for use in the field by those unskilled in the art of microbiology.

These problems increase the cost of obtaining a qualitative solution to the measurement of micro-organisms levels and provide no ability to realize a short term result.

The contamination of water, foodstuffs, additives, cosmetics, pharmaceuticals and the like by undesirable micro-organisms represents a significant threat to public health. In the past, a number of methods to monitor the presence of such micro-organisms in foodstuffs, water supplies and on food preparation surfaces have been developed.

Generally such methods rely on conventional microbiological techniques, typically including the growth of micro-organisms on selective nutrient solid support media or alternatively in selective nutrient media. Subsequent morphological and biochemical analyses are then carried out under laboratory conditions by skilled personnel.

One such technique currently carried out by the Applicant involves the use of a growth medium already stored in an evacuated UV light penetrative, clear plastics container that is sealed with a rubber septum.

The liquid sample to be tested is introduced into the container through the septum via a needle or some other form of cannulas, the pressure difference ensuring that the sample is "sucked" into the container. The sample is then incubated and tested for specific or broad types of microorganisms using visual techniques.

By necessity, some of these testing techniques tend to be carried out on products just before they are to be sent into the marketplace and these products cannot enter the market place until the results are back from the testing laboratories.

In respect of products for human consumption, some of the methods employed to remove any residual harmful micro-organisms have usually just taken place and thus, not too surprisingly, the level of micro-organisms that the testing techniques are designed to look for is so low that the test result for this micro-organisms is "negative". As such, the product is passed fit for human consumption.

However, the micro-organisms such as micro-organisms, yeast, or fungi, although present in un-detectably small quantities are nevertheless still present and multiply and under the right conditions, given the shelf life of the product, may be able to recover to the extent that the micro-organisms are suddenly present in sufficient quantity to cause harm once the product is consumed.

This problem of "shelf life recovery" is a serious one in many types of industry and very few solutions to this problem apart from limiting the shelf life of the product to a very small time frame have been proposed.

U.S. Pat. No. 5,728,542 by Charm et al. teaches the use of a flexible plastic bag with several compartments, to provide a simple test relying on the human eye to detect the presence or absence of colour in the bag.

Furthermore, the micro-organism testing kits (of the type described above) have relatively low shelf lives "out in the field" as UV light tends to kill the growth medium contained therein. In addition, the material once tested may or may not be a bio-hazard and disposal of such materials is expensive and legislation in this area is only ever going to increase the cost of disposal of such materials.

The present invention provides a solution to these and other problems which offers advantages over the prior art or which will at least provide the public with a useful choice.

DEFINITIONS

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

In this specification the term "sanitizer" is used to describe a material which is adapted to kill off or sanitize the contents of apparatus after testing has been completed. (I.e. any micro-organisms present).

"Transparent" in this specification means that the container (or at least part of it) is capable of allowing the passage of light beams through the container for testing purposes at the frequency bands used for testing, whether or not they are in or outside the visible spectrum.

OBJECT OF THE INVENTION

It is an object of the present invention to try to provide containers which unskilled personnel can use to take samples and test for the presence of micro-organisms, or which will at least provide the public with a useful choice.

STATEMENTS OF THE INVENTION

In one aspect the invention provides a container for testing micro-organisms, the container having a substantially rigid transparent chamber capable of retaining a liquid sample having a micro-organism growth promoter and a dye therein, the sample to be tested for the presence or absence of micro-organisms, the substantially rigid transparent chamber configured to allow a light beam to pass into the container and be measured by one or more light detectors, the container having a base and a removable cap to allow the insertion of a sample to be tested, a bactericidal chamber and a barrier separating the bactericidal chamber from the transparent chamber, said bactericidal chamber containing a sanitizer, and a barrier puncturing mechanism for releasing the sanitizer into the transparent chamber at the conclusion of the test.

Preferably the base contains the bactericidal chamber.

Preferably the barrier between the bactericidal chamber and the transparent chamber is a foil seal.

Preferably there is means for allowing the removable cap to be locked in place after the sample has been inserted to thereby prevent access to the sample and any micro-organisms it may contain.

In a further aspect the invention provides a container for testing micro-organisms, the container having a transparent chamber configured to allow a light beam to pass into the container and be measured by one or more light detectors, the container having a removable cap, a second chamber and a barrier separating the second chamber from the transparent chamber, the second chamber containing a growth promoter and/or a dye adapted to assist in detecting a presence or absence of micro-organisms, means for releasing the growth promoter and/or the dye into the transparent chamber, the container also including a third chamber and a barrier separating the second chamber from the transparent chamber, said third chamber containing a sanitizer, and a means for releasing the sanitizer into the container.

Preferably the barrier between the second chamber and the transparent chamber is a foil seal.

Preferably the barrier between the third chamber and the transparent chamber is a foil seal.

Preferably the cap is removable to allow for the insertion of a sample to be tested, and there is means for allowing the cap to be locked in place after the sample has been inserted.

Preferably the base contains the third chamber.

Preferably the container has a transparent cylindrical main portion, a base of one colour, and the cap of another colour to distinguish the contents of the base and cap.

Preferably the cap has a plunger which when depressed causes a serrated cutter within the second chamber to puncture the foil seal in the cap to release the contents to commence testing for micro-organisms.

Preferably the base has a plunger which when depressed causes a serrated cutter within the third chamber to puncture the foil seal in the base to release the sanitizer.

Preferably the or each plunger has a resilient convex outer surface which sits inboard of the lid or base to prevent accidental depression of either of them.

In another aspect the invention provides a set of containers for testing micro-organisms, each container being of a same size and shape as the other containers, each container having a transparent portion configured to allow a light beam to pass into the container and be measured by one or more light detectors, to provide an electric output, each container having a removable cap, the removable cap having a first compartment in the cap defined by a size of the cap, and a foil seal, the first compartment containing a growth promoter and/or a dye adapted to detect a presence or absence of micro-organisms, the cap also including means to enable the foil layer to be punctured to release the contents of that compartment, each container also including a separate compartment containing a sanitizer, and means for releasing the sanitizer into the container.

Preferably the sanitizer compartment is situated in the base of the container.

Preferably the cap of each container is of a first colour designating the growth promoter compartment; and the base of each container is of a second contrasting colour designating the sanitizer compartment.

Preferably the or each plunger has a resilient convex outer surface which sits inboard of the cap or base to prevent accidental depression of either of them.

Preferably the container apparatus has at least three compartments, the third containing a further additive adapted to kill off or sanitize the contents of the apparatus after testing has been completed (called "the sanitizer"). In most cases this will involve a material which is toxic to all micro-organisms such as bleach.

Preferably the container comprises a barrier puncture mechanism adapted to move from a first barrier intact position to a second barrier punctured position Preferably the barrier puncture mechanism is provided with a locking member adapted to lock the mechanism in its first position.

The inventive concept is based on the realisation that a colour change in a growing sample in this type of container can be easily carried out automatically in an incubator with built in light detection apparatus and comparing the measured colour changes over time with stored information of the colour change over time of samples of known micro-organisms.

Preferably the sanitizer is an agent (for example bleach or a product known by the Registered Trade Mark VERKON®) capable of killing the micro-organisms within the container. As such, the biohazard problem can, in principle, be 'reduced' or eliminated entirely.

Although the resealable nature of the container could be something as simple as a rubber septum, it is preferable if it were some form of removable lid. If the septum variant is employed, a moveable cannula could be fitted to the apparatus inside a sleeve that is fits over the septum to allow safe use of the cannula when using it to pass a sample into the apparatus.

Preferably the apparatus has at least three compartments, the third containing a further additive. This further additive may include micro-organisms. This would be useful if the test sample is milk. If antibiotics are present in the milk, the micro-organisms may be killed by the antibiotics providing a test result for the presence of the antibiotic but if the micro-organisms flourish, then the milk sample may be viewed as antibiotic free. This demonstrates a test involving (but not for) micro-organisms. Alternatively, this additive may include a bacterium or micro-organisms specific detector, growth promotant, selective growth promotant, growth metabolic or biochemical indicator selective growth agent and a non specific container sterilizing medium.

More preferably still the apparatus comprises a tubular body portion provided with screw threads at either end and two closure members each containing complementary screw threads and each containing a compartment (sealed by one or more barriers), housing at least one additive and a similar number of barrier removal or puncture mechanism.

The removal of the barrier could for example constitute a pair of apertured completely overlying concentric rotatable discs where in one position the apertures of one disc do not overlie the apertures of the second disc thus presenting a "sealed" barrier and upon rotation of one disc relative to the other, at least some of the apertures align removing the "sealed" nature of the barrier to allow either the growth medium or additive to enter the rest of the apparatus. Alternatively, the barrier may simply be removable by tearing it off.

Preferably however, the apparatus comprises a barrier puncture mechanism adapted to move from a first barrier intact position to a second barrier punctured position.

Such a mechanism may be resilient so that once it has been moved from its first to its second position; it can recover and return automatically to its first position again.

For example if the barrier comprises two discs incorporating surfaces that may act as blades, the rotation of the discs could cause the barrier (if it were made of foil) to tear. However, more preferably, the movement of the puncture mechanism is a translational movement. This does not necessarily mean that actuation of the puncture mechanism is through a translational movement (although it probably will be), one could envisage a scenario whereby rotation of the puncture mechanism causes it to move in a translational direction, similar to the rotary action of a domestic tap that causes the spindle to move translational manner to enable water to flow.

As premature barrier removal is undesirable, preferably, the barrier puncture mechanism is provided with means to prevent accidental actuation of the mechanism.

These means could take the form of physical covers that wholly encase the puncture mechanism, a barrier or wall that offers only partial protection or a locking member.

More preferably, the means are in the form of a locking member adapted to lock the mechanism in its first position.

There may be multiple barriers or only one (if it were to comprise a pair of wells one housing the growth medium and the other housing an additive), however, preferably there is more than one barrier.

More preferably still, there is more than one barrier puncture mechanism (which may or may not be identical in design to the first). If there are two, they may be located at opposite ends of the apparatus.

The additive may be a so-called controlled release additive. Alternatively, it could be a timed release additive in the sense that a barrier puncture mechanism could be so operatively connected to the apparatus as to puncture a barrier containing additive after a timed delay via a "press and forget" system which a person skilled in the art would be able to design.

The additive may be in the form of a tablet, a powder, a liquid or a strip of material impregnated with the additive through liquid absorption or adsorption.

Preferably there is more than one additive. The design of the apparatus could be such that once an additive has been added via the removal of a barrier; access to the interior of the container would not normally be possible. Alternatively, the apparatus could be provided with a lockable lid that could only be locked once a lock prevention device has been removed from the apparatus. This lock prevention device could be a barrier in the form of a tub or cup or removable gasket.

More preferably, each additive is enclosed within its own barrier and its own barrier puncture or removal mechanism.

For the avoidance of doubt, "growth promotant" means anything that enables micro-organisms to grow or provide an environment in which more rapid growth can occur and typical growth promotants include water, sugars, peptones and particulate matter. Furthermore, and again for the avoidance of doubt, a selective growth agent includes one which either inhibits growth of all the micro-organisms that is not the subject of investigation or is specifically required by the species being investigated for growth and typical selective growth agents include sodium chloride and bile salts or selective antibiotics. Typical growth indicators include resazurin, fluorescein and brilliant green.

Yet more preferably, each barrier puncture mechanism once actuated, is adapted to release a separate additive.

Although the apparatus could comprise many types of plastics or glass material, it is preferable if the body of the apparatus absorbs UV light and does not allow it to pass through the apparatus.

Preferably the apparatus incorporates a swab that may or may not be integral with part of the apparatus and which may or may not be supplied with a wetting agent which may be a non specific growth medium.

Preferably the apparatus is provided with a mesh or sieve to filter or trap solid particles of a test specimen whilst allowing the growth medium to interact with the specimen.

Although it may be removable for cleaning purposes, it would be more preferable if the mesh or sieve is integrally locked or forms an integral part of the apparatus.

Preferably the mesh size is in the range of 25-250 microns, more preferably 70-200 microns.

The micro-organism under test could be fungi, yeast or protozoa; however, preferably the micro-organism that is going to be tested for is a bacterium or a number of different strains of micro-organisms.

The invention includes within its scope micro-organism testing apparatus substantially as herein described with reference to and as illustrated in the accompanying drawings.

The invention also includes within its scope a testing apparatus fitted with one or more microorganism testing apparatus's as specified herein The testing apparatus may be adapted to warm the test sample up to 37 degrees or more.

According to a second aspect of the present invention, there is provided a method of testing for or at least using one type of micro-organism using a micro-organism testing apparatus of the type specified herein and comprising the steps of:

unsealing a container to gain access to its interior and adding a sample to be tested to a growth medium present in the container;

resealing the container and subsequently allowing the growth medium and sample to mix;

visually checking for a colour change in the solution;

removing a barrier to allow an additive to kill the micro-organisms present within the container.

Although a visual check may be all that is necessary to see whether one or more microorganisms is/are present, it may be preferable to place the apparatus into additional testing apparatus adapted to test for the presence of the micro-organism via a more sensitive means.

Preferably the micro-organism is a bacterium.

According to a third aspect of the present invention, there is provided a method of testing for at least one type of micro-organism comprising the steps of:

Unsealing a container of the type specified herein to gain access to at least one barrier of the container that separates compartments within the container, one compartment containing a micro-organism testing agent:

adding a sample to be tested to the container adding a growth medium to the container;

resealing the container and subsequently allowing the growth medium, sample and micro-organism testing agent to mix;

testing for the presence of the micro-organism and subsequently adding an additive to the container to kill the micro-organisms present within it.

Unsealing the container may be achieved through the puncturing of a rubber septum. Preferably the barrier is removed by puncturing it. Preferably, the growth medium is an aqueous growth medium.

The method further includes the step of placing the apparatus into the test apparatus to obtain the test results.

The apparatus and the methods of testing described herein provide a self contained kit for testing material that does not require the use of a laboratory, can combine tests for multiple types of micro-organisms in the same piece of apparatus and is simple to use (you do not need to be a trained scientist to use or indeed understand how to use the apparatus) and is safe to use.

This is because an operator after sealing the apparatus with the test sample inside is probably not going to be able to open the apparatus again so the mixing of additives/growth promoters etc. is all self-contained and there is no possibility of the contents spilling out and contaminating the tester or the environment.

Finally, the tested material can be sanitized or rendered safe, again without the tester being able to contact the tested sample.

The invention includes within its scope methods substantially as described herein with reference to and as illustrated in any appropriate selection or combination of the accompanying drawings.

BRIEF DESCRIPTION OF THE DRAWINGS

Preferred embodiments of the present invention will now be more particularly described, by way of example only, with reference to the accompanying sheets of drawings in which.

DESCRIPTION OF THE PREFERRED EMBODIMENTS

Example 1

Container

Figure 1:
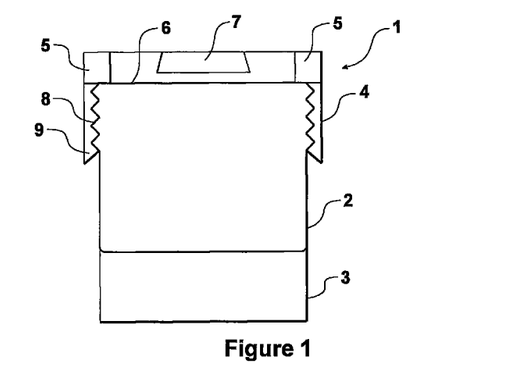
FIG. 1 illustrates a sectional side view of one embodiment of the present invention.

FIG. 1 shows one embodiment of a bacterium testing apparatus comprising a screw threaded container generally referenced 1. The container 1 comprises a rigid body 2 containing an aqueous growth medium 3 and a lid 4. The internal face of the lid 4 about its circumferential periphery is provided with resilient wadding 5 adapted to create a water tight barrier with the body 2 when the lid 4 is tightly screwed to the body 2 via the mating threads 8.

A foil seal 6 overlies and mates with the circumferential peripheral face or mouth of the body 2 in a watertight manner. The barrier 6 is provided with a tag 9 (that reveals itself when the lid 4 is removed), to enable the barrier 6 to be removed from the mouth of the body 2 of the container 1 when the lid 2 has been unscrewed from the body 2.

Substantially centrally located on the internal face of the lid 4 is a circular sheet of filter paper 7 impregnated with a bacterium testing agent.

Operation of the apparatus 1 is as follows;

The lid 4 is unscrewed from the body 2 by an individual (not illustrated) who is about to perform the micro-organism test. Then the individual grabs the tag 9 and pulling the tag 9 swiftly across the mouth of the body of the container 2 removes the barrier 6 exposing the growth medium 3 held within the body 2 of the container 1 for the first time.

The sample to be tested (not illustrated) in this particular example is milk powder and the tester is going to be looking for coliform micro-organisms. The sample is then placed into the medium 3 and the lid 4 screwed tightly back onto the body 2 of the container 1, the resilient wadding 5 forming a watertight barrier for the container 1.

Subsequent inversion or shaking of the container 1 causes mixing of the bacterium testing agent with the growth medium/sample mixture or growth medium solvent/dissolved sample solute. The container 1 is then placed in an incubator and warmed to 37 degrees for an adequate passage of time. Removal of the container 1 and a visual check of the growth medium 3 will tell whether the bacterium is present because the growth medium will have experienced a visible colour change.

Example 2

Container with Single Plunger

Figure 2:
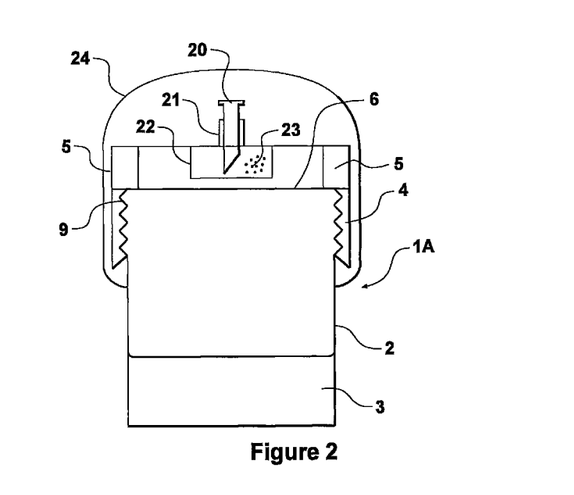
FIG. 2 illustrates a sectional side view of another embodiment of the present invention.

FIG. 2 shows a different embodiment to that shown in FIG. 1 although the general features of the apparatus generally referenced 1A are the same as previously described hereinabove. However, in this particular embodiment, instead of a piece of filter paper impregnated with a bacterium testing agent, there is provided a cylindrical foil pocket 22 containing a bacterium testing agent 23.

Again, the pocket 22 is centrally located on the internal face of the lid 4, with the mouth of the pocket 22 permanently sealed to the internal face of the lid 4. Concentric with the pocket 22 and located on the exterior surface of the lid 4 is an upwardly projecting sleeve 21 that acts as a guide for and houses a sliding plunger 20. The top of the plunger 20 is provided with a flange that overlies the sleeve 21 and acts as a stop member to prevent the plunger 20 from moving beyond a certain point when depressed and the base portion of the plunger 20 is provided with a cutting edge to puncture the base of the pocket 22 when it is depressed.

Surrounding the lid 4 is a relatively inflexible plastics bubble 24 sealed to the container 1A below the screw thread 8 that acts as a physical guard against the accidental depression of the plunger 20. This "guard" 24 also acts as a visual tamper proof check to see if the container 1A has already been opened.

Operation of the apparatus 1A is as follows:

The guard 24 is broken and subsequently removed by an individual (not illustrated) who is about to perform the micro-organism test. Then the lid 4 is unscrewed from the body 2 by the individual. Then the individual grabs the tag 9 and pulling the tag 9 swiftly across the mouth of the body of the container 2 removes the barrier 6 exposing the growth medium 3 held within the body 2 of the container 1A for the first time.

The item to be tested (not illustrated) is then placed into the medium 3 and the lid 4 screwed tightly back onto the body 2 of the container 1A, the resilient wadding 5 forming a watertight barrier for the container 1A.

The plunger 20 is then depressed puncturing the pocket 22 and allowing the pocket's contents 23 to mix with the growth medium 3 and sample.

Subsequent inversion or shaking of the container 1A causes further mixing of the bacterium testing agent 23 with the growth medium/sample mixture or growth medium solvent/dissolved sample solute. The container 1A is then placed in an incubator and warmed to 37 degrees for a sufficient time period. Removal of the container 1A and a visual check of the growth medium 3 will tell whether the bacterium that is being tested for is present because the growth medium will have experienced a visible colour change.

Example 3

Container with Dual Plunger

Figure 3:
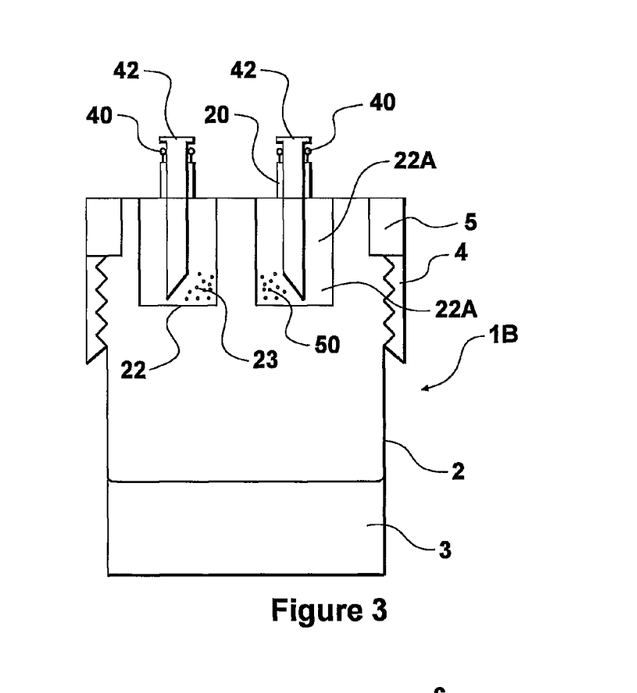
FIG. 3 illustrates a sectional side view of yet another embodiment of the present invention.

FIG. 3 shows a different embodiment to that shown in FIGS. 1 & 2 although the general features of the apparatus generally referenced 1B are the same as previously described in FIG. 2.

However, in this particular embodiment, instead of a single plunger, the lid 4 possesses a pair of plungers 42 arranged in side by side relationship and instead of the guard being in the form of a bubble, each plunger is provided with a removable clip 40 located in the space between the top of the sleeve 20 and the base of the flange. The clip 40 prevents depression of the plunger until it is removed.

Furthermore, in this embodiment, the barrier 6 is not present. One of the plungers 42 contains a second bacterium testing agent 50 adapted to test for another subset of microorganisms after the first test using the other plunger 42 has been carried out.

Operation of the apparatus 1B is as follows:

The clips 40 are removed by an individual (not illustrated) who is about to perform the micro-organism test. Then the lid 4 is unscrewed from the body 2 by the individual, exposing the growth medium 3 held within the body 2 of the container 1B for the first time. The item to be tested (not illustrated) is then placed into the medium 3 and the lid 4 screwed tightly back onto the body 2 of the container 1B, the resilient wadding 5 forming a watertight barrier for the container IB. The container 1B is then placed in an incubator and warmed to 37 degrees for an adequate time period.

The plunger 42 is then depressed puncturing the pocket 22 and allowing the pocket's contents 23 to mix with the growth medium 3.

Subsequent inversion or shaking of the container 1B causes further mixing of the bacterium testing agent 23 with the growth medium/sample mixture or growth medium solvent/dissolved sample solute. Removal of the container 1B from the incubator and a visual check of the growth medium 3 will tell whether the bacterium that is being tested for is present because the growth medium will have experienced a visible colour change.

Once this test has been completed, the container 1B is removed from the incubator.

The other plunger 42 is depressed puncturing the pocket 22A and allowing the pocket's contents 50 to mix with the contents of the container IB.

Subsequent inversion or shaking of the container 1B causes further mixing of the bacterium testing agent 50 with the container 1B contents. Again, the container is placed in the incubator and heated to a sufficient temperature for a sufficient time period.

Removal of the container 1B from the incubator and a visual check of the growth medium 3 will tell whether this second bacterium that is being tested for is present because the effect of the presence of this other bacterium in the presence of the contents 50 will produce another colour change.

Example 4

Container with Modified Base

Figure 4:
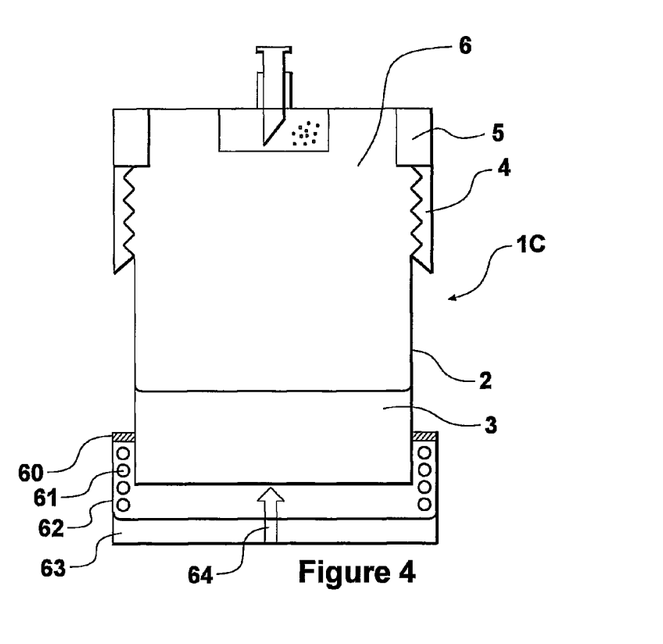
FIG. 4 illustrates a sectional side view of a further embodiment of the present invention.

FIG. 4 shows a different embodiment to that shown in the other figures although the general features of the apparatus generally referenced 1C are the same as previously described in FIG. 2.

However, in this particular embodiment, there is no guard. Furthermore, in this embodiment, the barrier 6 is not present. The base of the container 1C however, is provided with a spring loaded 61 sealed 60 bleach containing 63 reservoir with a tang 64 adapted to break the base of the container 1C allowing the contents of the container 1C to mix with the bleaching agent 63 to kill the live contents of the container 1C after the test has been completed thus dispensing with the need to incinerate the apparatus 1C post testing.

Operation of the apparatus 1C is as follows:

The lid 4 is unscrewed from the body 2 by an individual (not illustrated) who is about to perform the micro-organism test exposing the growth medium 3 held within the body 2 of the container 1C for the first time. The item to be tested (not illustrated) is then placed into the medium 3 and the lid 4 screwed tightly back onto the body 2 of the container 1C, the resilient wadding 5 forming a watertight barrier for the container 1C.

The plunger 20 is then depressed puncturing the pocket 22 and allowing the pocket's contents 23 to mix with the growth medium 3.

Subsequent inversion or shaking of the container 1C causes further mixing of the bacterium testing agent 23 with the growth medium/sample mixture or growth medium solvent/dissolved sample solute. The container 1C is then placed in an incubator and warmed to 37 degrees for an adequate time period. Removal of the container 1C and a visual check of the growth medium 3 will tell whether the bacterium that is being tested for is present because the growth medium will have experienced a visible colour change.

Once the test is over the lid 4 becomes the plunger and the container 1C is pushed onto the tang 64 until the base (and only the base) of the container 1C ruptures allowing the contents of the container 1C to mix with the bleach killing the entire contents of the container 1C allowing it to be disposed of safely.

Example 5

Transparent Container with Coloured Lid

FIGS. 5 to 8 show this example in detail and help to explain how it is to be used.

Figure 5:
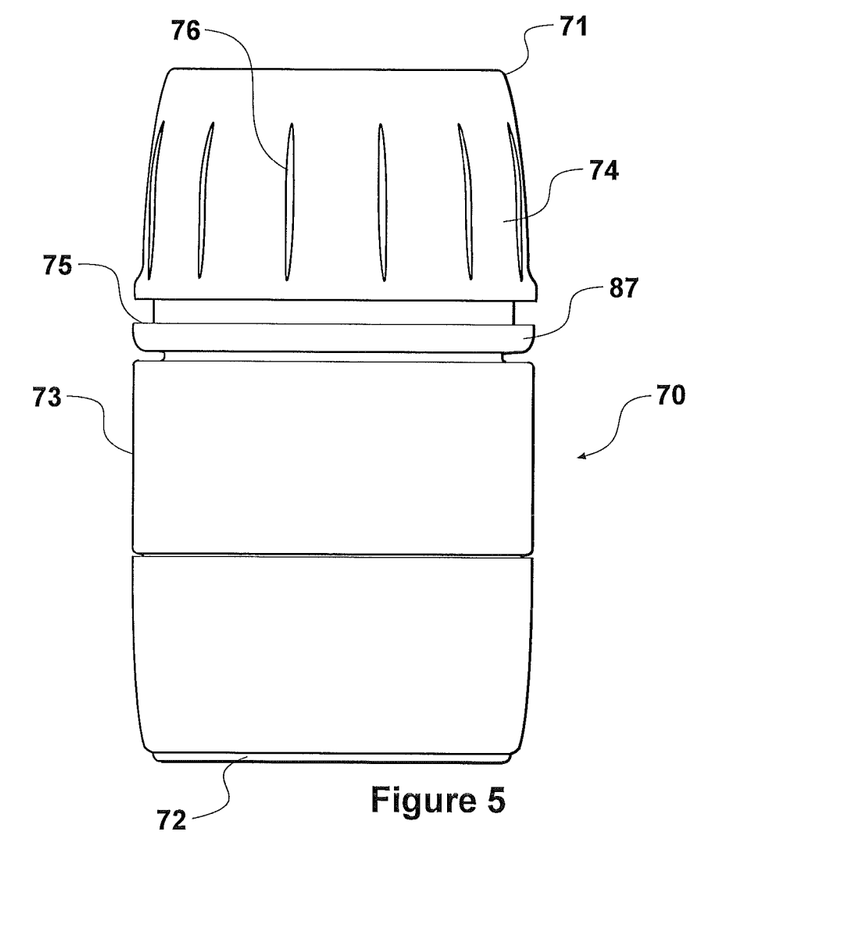
FIG. 5 illustrates a side view of another embodiment of the present invention.

FIG. 5 shows a side view of a columnar micro-organism testing apparatus comprising a screw threaded container that is generally referenced 70, and the central portion is substantially rigid and transparent to allow light to pass through when in the incubator described below.

The apparatus 71 comprises a top portion in the form of a lockable lid 71, made from blue polyethylene, to serve as a visual indicator to a user of the apparatus 70 of the type of growth medium (and hence the type of test that is going to be carried out) is located therein, a base portion 72 again made from polyethylene, but this time the plastics material used is coloured pink to serve as a visual indicator to the user that this is the end that contains a killing agent, and a central body portion 73 formed from UV absorbing (i.e. non penetrative) plastics material.

From the side, the lid 71 is in the form of a truncated dome incorporating a flange base. The lid 71 is provided with a twelve elongate, parallel spaced apart completely overlying ribs 76 whose longitudinal axes are parallel with the longitudinal axis of the assembled apparatus 70. Each rib 76 begins in the flange base and terminates prior to the truncated top of the lid 71 and they serve as a finger grip when a user handles the apparatus 70.

Figure 6:
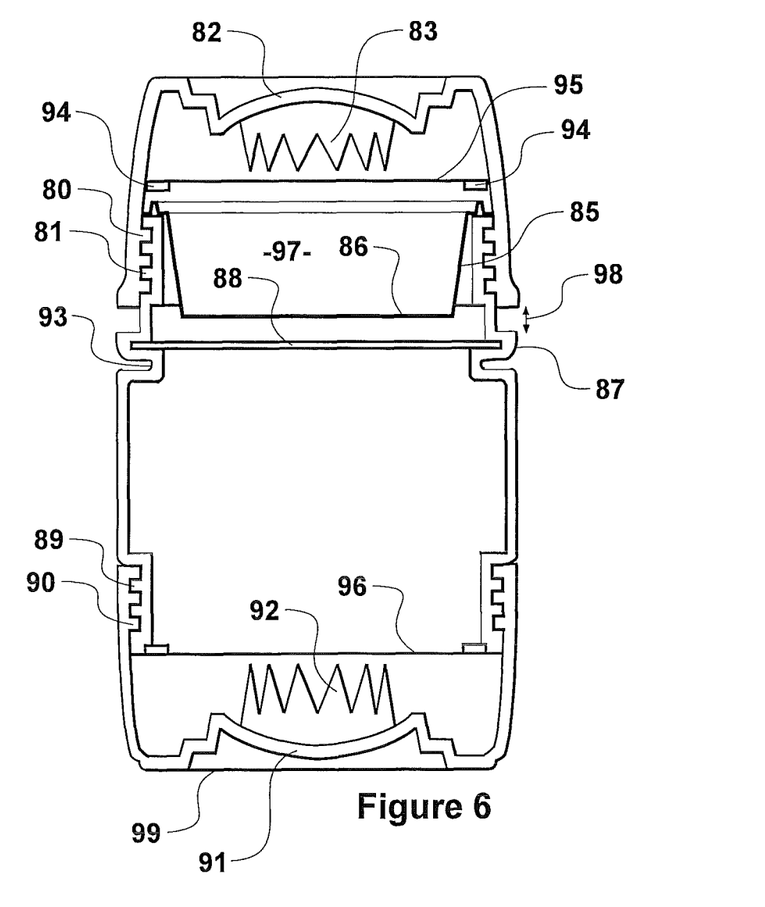
FIG. 6 illustrates a sectional side view of the embodiment illustrated in FIG. 5.

Turning to FIG. 6, this shows a cross section of the embodiment shown in FIG. 5 and as can be seen, the lid 71 mates with the body 73 via complementary screw threads 80, 81 located around the respective necks of the lid 71 and body 73. A black natural rubber tub 84,85,86 of uniform thickness comprising an annular flange top 84, integral with a continuous linear sloping side wall 85 that is to all intents and purposes, frusto-conical in shape and which terminates in a flat circular base 86 that is concentric with, is smaller than and parallel with, the flange top 84.

The flange top 84 is so designed as to overlie the thickness of the top of the neck of the body 73, whilst the base 86 is substantially flush with bottom of the neck of the body 73.

The flange top 84 prevents the lid 71 from being screwed down completely onto the threaded 81 neck of the body 73 of the apparatus 70.

The lid 71 is provided with a resilient circular convex diaphragm 82, the centre of which passes through the longitudinal axis of the apparatus 70. This centre sits below the truncated top of the lid 71 to prevent accidental depression of the top 82 if something that can span the lid top comes to rest on the truncated top of the lid 71.

The underside of the diaphragm 82 is operatively connected to a downwardly depending and expanding frusto-conical wall terminated by a plurality of "saw tooth" shaped teeth 83 that are adapted to puncture a circular foil sheet 95 that is glued to and which spans the upper portion of the interior of the lid 71 above the flange top 84 to form a separate integral compartment within the lid 71.

The compartment contains a specific type of growth medium.

Centrally located, glued to and downwardly depending from the foil 95 is an annular shaped testing swab sponge 97 whose dimensions are such that it extends down to substantially contact the base 86 and occupy a large volume of the tub 84,85,86. The tub 84, 85, 86 contains sufficient amounts of a non specific growth medium to wet the sponge 97.

Sandwiched between the foil sheet 95 and the top of the flange top 84 is a plastics "O" ring 94 that substantially overlies the annulus of the flange top 84.

Moving from the top of the apparatus 70 in a downward direction in the apparatus's initial attitude of operation, immediately below the screw threaded 81 neck of the body 73, is a wider concentric flange shoulder 87 that is immediately followed by a concentric constriction 93, which then widens once again to substantially the same dimensions as the shoulder 87, to form the main part of the columnar body 73 of the apparatus 71.

Trapped within the internal thickness of the shoulder 87 is a flat circular filter 88 that spans the entire surface area swept out by the internal thickness of the shoulder 87. The distance separating the bottom of the flange base of the lid 71 from a top surface 75 of the shoulder 87 is substantially equal to the thickness of the flange top 84.

The base portion 72 mates with the body 73 via complementary screw threads 89,90 located around the respective base necks of the base portion 72 and the body 73 in a lockable manner and is usually supplied pre-locked into place.

A resilient circular convex diaphragm 91 mirroring that of the top 82 and provided with a similar set of teeth 92 as that of the diaphragm 82 is located within the base portion 72. The teeth 92 are adapted to puncture a circular foil sheet 96 that is glued to and which spans the start of the base neck of the body 73 to form a separate integral compartment within the base portion 72.

The centre of the diaphragm 91 is recessed within the flat base 99 of the base portion 72 so that accidental depression of the diaphragm 91 if something that can span the base 99 comes to rest on base 99 during for example transit of the apparatus 70, does not occur.

This compartment located within the base portion 72 contains bleach.

Figure 7:
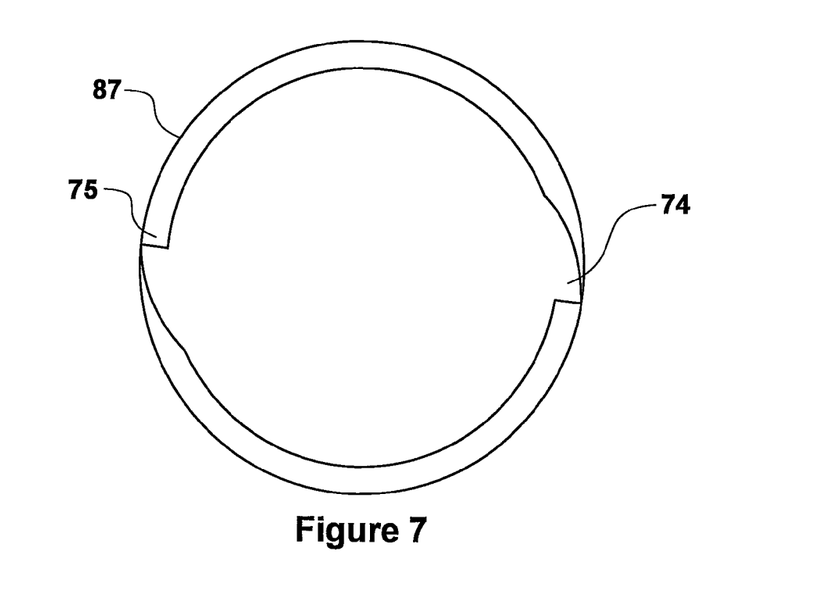
FIG. 7 illustrates a top view of a locking mechanism used to lock a lid to a body of the embodiment illustrated in FIG. 5.

Turning now to FIG. 7, this is a top view of the shoulder 87 in its initial normal attitude of operation and the figure also shows the area immediately above the shoulder 87, i.e. the area immediately below the start of the screw threaded neck 81 of the body 73. Integral with and sat on the uppermost surface 75 of the shoulder 87 is a curved shoulder 74 (similar in shape to a leading edge of a shark fin) whose radius of curvature has a centre that is not the same as the centre of the radius of curvature of the apparatus 70 but is parallel with it. The shoulder 74 extends as a continuous curve from the base of the exterior surface of the neck 81 and terminates abruptly with a straight line that overlies a virtual diameter of the apparatus 74.

Opposite the shoulder 74 on the same upper surface of the shoulder 87 is a similar shoulder 74. This similar shoulder 74 is located at a point that is a 180 degree rotation of the first shoulder 74 about the centre of the apparatus 70. The thickness of both shoulders 74 is slightly less than the thickness of the flange top 84.

Figure 8:
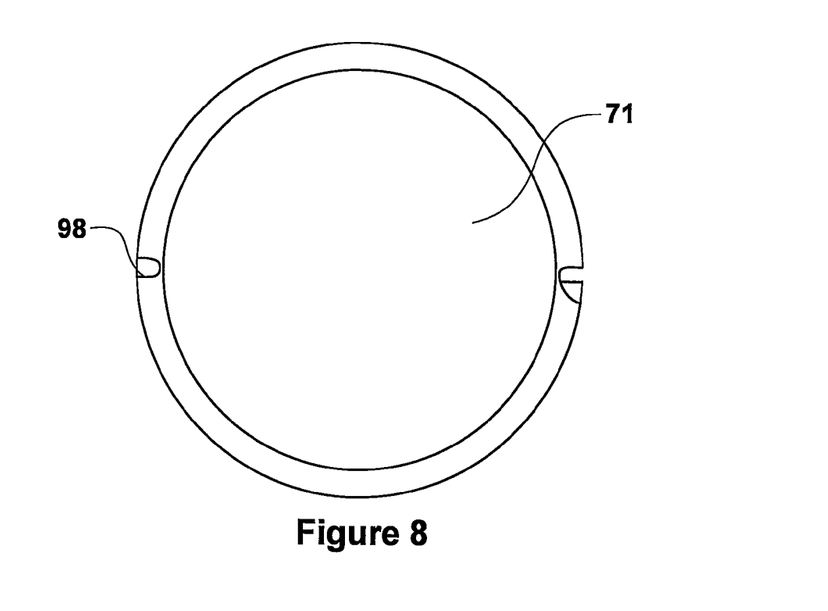
FIG. 8 illustrates an underside view of a base of the lid illustrating a complementary locking mechanism to that illustrated in FIG. 7.

FIG. 8 shows the underside of the flange base of the lid 71 Projecting radially inwards from the internal circumferential peripheral wall of the base of the flange base, are a pair of mutually opposed elongate resilient "shark fin" shaped nipples 98 that are of a similar thickness to the thickness of the shoulders 74. The nipples 98 extend inwardly, decreasing in size until they would substantially contact the screw thread 81 at which point they terminate.

The leading edge of each "shark fin" is designed to contact respective curved shoulders 74 as the lid 71 is screwed down fully.

In use, the lid 71 is unscrewed and the tub 84, 85, 86 is first removed.

The lid 71 and the non specific growth medium impregnated sponge 97 combination is used to swab the test surface for micro-organisms.

Aqueous growth media is added to the body 73 of the apparatus 70 The lid 71 (free from the tub 84, 85, 86) is fully screwed back over the neck of the body 73.

The last turn of the lid 71 causing the curved nipples 98 to ride over the curved shoulders 74 and snap back to their start position so that substantially the "flat" side of the shoulders 74 now contact the trailing edges of the nipples 98 thus making it normally not possible to unscrew the lid 71 and effectively locking the lid 71 to the body 73 so that the contents of the apparatus 70 cannot escape. At this point, the 0 ring 94 becomes compressed between the thickness of the top of the neck of the body 73 and the internal top of the lid 71 to from a substantially fluid tight barrier for the apparatus 70.

The convex top 82 is then depressed by a thumb of an operator and the teeth 83 puncture the foil 95 to release the growth medium.

The apparatus 70 is then inverted and in this state is placed into a micro-organism testing machine where it is incubated and scanned with a range of light wave lengths to detect the presence of micro-organisms.

At the end of the test, the convex base 92 is depressed causing the teeth 92 to puncture the foil 96 to enable the bleach to enter the body 73 and kill all of the micro-biological material within it.

If the apparatus 70 is to be used to test a solid product such as meat, the apparatus 70 water is pre supplied in the apparatus 70. The meat sample is placed within the neck of the body 71 and the lid 71 is screwed down tight as before. Puncturing of the foil 95 and shaking of the apparatus 70 will cause the meat to mix with the growth medium but the filter 88 will prevent lumps of meat from entering the body 73 of the apparatus 70, 'clouding' the test solution and causing erroneous readings during the testing procedure. Inversion of the apparatus 70 prior to placing it within the incubating microorganism testing machine will ensure that the meat through gravity will sit within the base of the lid 71 and not tend to potentially diffuse through the filter 88 to cause erroneous results.

Once testing has been completed and the microbiological material killed the apparatus can be sent for normal disposal.

By providing a standard set of containers of identical size and shape, each provided with a calibrated amount of the same growth promoter and/or dye the containers can be calibrated against known micro-organism samples. Some of the containers may be provided with sterile water within the main body (for reception of a solid or powder sample, e.g. milk powder, meat, shellfish, etc.). In other cases the main body may be empty so that a water sample can be collected e.g. from a river. In all cases it is preferable to sterilize the container and the ingredients to minimize the risk of micro-organism contamination during preparation or storage of the containers.

Example 6

The Incubator

Figure 9:
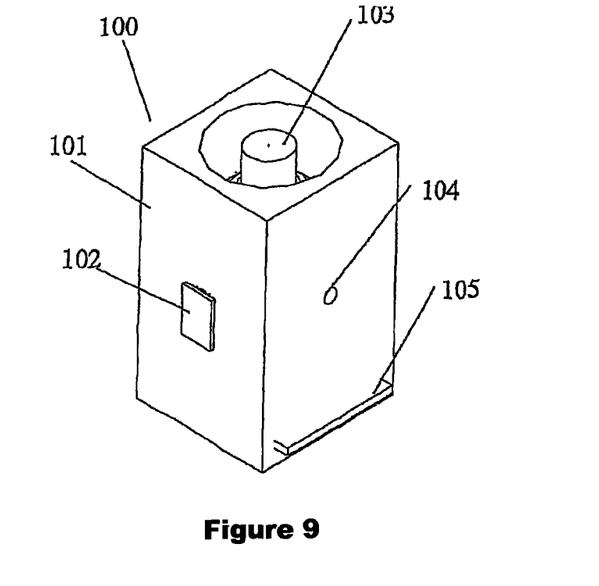
FIG. 9 is a general perspective view of an analytical apparatus according to the parent invention and having a void for reception of the containers illustrated above.
Figure 10:
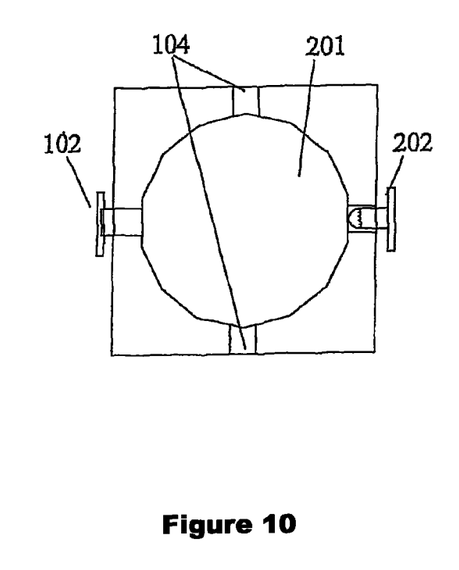
FIG. 10 is a top view of the apparatus of FIG. 9.
Figure 11:
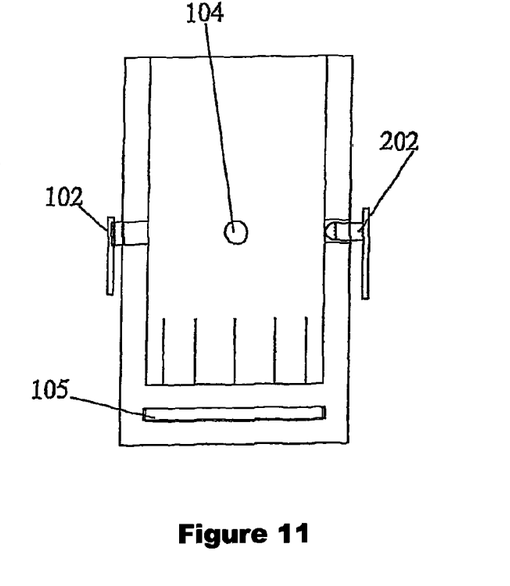
FIG. 11 is a side cross-section of the apparatus of FIG. 9.

FIGS. 9 to 11 illustrate an incubator with built in detection equipment designed to receive the containers of this invention.

Referring now to FIG. 9 an optical measurement apparatus 100 is shown. The apparatus includes a heating block 101, typically of aluminium, an optical sensor 102 mounted on a printed circuit board, a light source 202 (obscured) and a transparent vial 103 of fluid (of the type described in Examples 1 to 5) containing potentially measurable micro-organisms in a medium which shows a colour change on growth of the micro-organism to be detected. The heating block 101 has at least two and possibly four holes 104 which allow light from an opposing light source to pass through the vial. An inserted resistive heater 105 is also provided.

The vial contains a fluid, normally water, which may be contaminated with micro-organisms such as coliform micro-organisms, or which may contain substance which may possibly be contaminated, such as macerated shellfish. A detection agent is placed in the fluid, typically a dye such as Methylene Blue or Resazurin. There may additionally be placed in the fluid agents to provide nutrients to the micro-organisms and suppressants, to suppress growth of microorganisms which may compete with the wanted micro-organism. With the dye or indicator, as the micro-organisms grow the dye or indicator may be reduced or otherwise chemically altered in the liquid causes a change in colour, for methylene blue from blue to colourless and for Resazurin from violet to pink. It is not necessary that a dye which changes colour with a reduction reaction is present, so long as there will be a colour change in the fluid as the microorganism of interest grows. This may be caused by an indicator whose structure is changed by the micro-organism to provide some optical change in the liquid, or it may be caused by the growth of the micro-organism itself.

The optical sensor 102 is a colour sensor. It is preferably RGB sensitive and may also be UV sensitive. A typical sensor of this type is the TCS230, manufactured by Texas Instruments Ltd and marketed by Texas Advanced Optoelectronic Solutions Inc, which can produce an indication of the incident light level in the white, red, green and blue optical bands. The sensor is also UV and infrared sensitive to some extent, though normally a UV filter may be fitted to prevent any UV light from producing an output. The major advantage of using such a sensor is that the detection diodes are formed simultaneously on the same substrate, being differentiated only by the filter in front of the detectors and are therefore balanced.

The light source 202 is a source having output in the colour bands of interest. Typically it may be a white or blue LED, and is mounted on a printed circuit board. The beam width of the LED is preferably small, between 5 and 15 degrees being desirable.

FIG. 10 shows holes 104 through which the vial may be seen, LED 202 projecting into one of the holes and transmitting light to sensor 102.

FIG. 11 shows a side view of the apparatus and the inserted heater 105. The temperature of the block may be sensed either by the variation in the resistance of the heater with temperature, or from a separate thermistor (not shown). Power to the heater is continuously controlled in accordance with the detected temperature to maintain the temperature of the fluid in the vial sensibly constant. The choice of temperature is governed by the organism it is wished to culture, since different organisms have markedly different growth rates at slightly different temperatures. Typically the power to the heater is a pulse width modulated waveform, with the pulse width varied inversely in accordance with the temperature, and the temperature is controlled to better than 1° C.

In operation a vial 103 containing the fluid suspected of being contaminated is treated with the dye of choice and inserted in the apparatus. The output in each of the RGB bands, and possibly in white light is recorded as a starting point and changes in the relative output at each band are monitored. The transmitted light is continually monitored until a colour change becomes evident or until the required time has elapsed. There are two possible scenarios.

Firstly there may be no contamination, in which case there will be little change in colour within the specified time.

Secondly there may be contamination with the suspected organism and a colour change of the expected type will occur. This may be automatically detected by a supervising program which cyclically checks the detected colour and luminance and analyses it.

To attempt to provide some resolution of the type of contamination a further LED may be placed in a hole 104 with its light projected at 90 degrees to the sensor. Light from the LED is alternated with light from an LED 202 and provides a measure of reflected light from the organisms or other contents of the fluid. Again, the results obtained will depend on the growth pattern of the organism and the organism per se, but a comparison of the two results will allow close identification of the organism or organisms concerned.

Example 7

Calibration Graphs

FIG. 12A to 12D shows typical results for a series of tests showing in each the red, green and blue visible bands. In addition to this the turbidity of the fluid is indicated by measuring the backscatter from a side illuminating LED in hole 104. The vertical scale in FIGS. 12A to 12D is of the relative luminance of light from the container, the horizontal scale is in minutes.

Figure 12A:
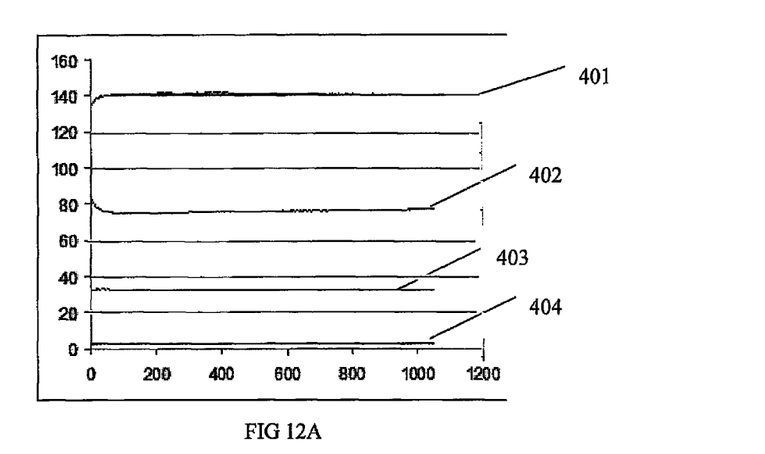
FIG. 12 shows various graphs (12A to 12D) of colour transmission in a fluid medium.

FIG. 12A shows the results for a test in which there are no micro-organisms present. The graph shows little change with time in either the red 401, green 402, blue 403 or turbidity 404.

Figure 12B:
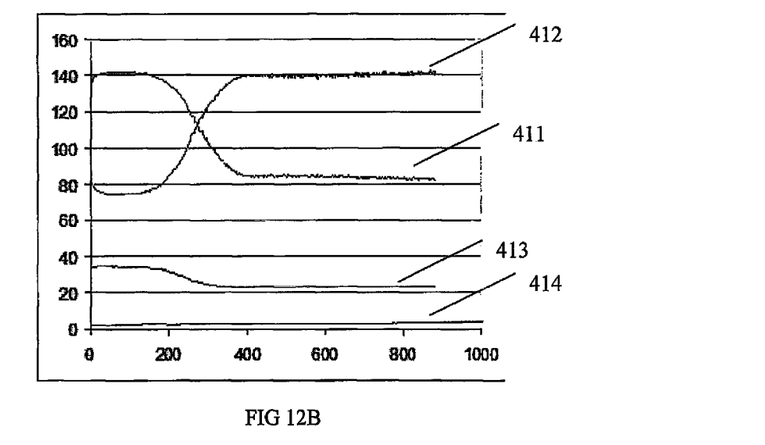

FIG. 12B shows results for one type of coliform micro-organisms showing a steady conversion from red to blue at 411, 412, associated with a slight drop in green 413 and practically no change in turbidity 414.

Figure 12C:
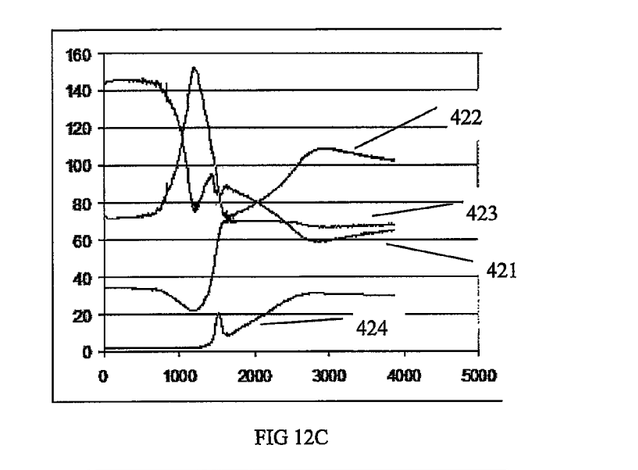

FIG. 12C shows the results for a differing coliform micro-organisms where a sharp rise in turbidity 424 is accompanied by a sharp drop in blue 421, a rise in red 422 is immediately followed by a sharp rise in green 423 and a steady increase in turbidity 414.

Figure 12D:
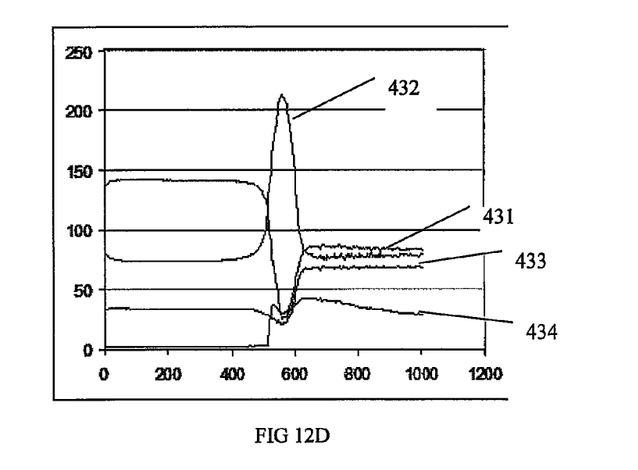

FIG. 12D shows yet another type of coliform micro-organisms in which the blue 431 degrades while red 432 shows a sharp rise followed by a fast degradation. Green transmission 433 shows an abrupt rise associated with the drop in red, while the turbidity 434 shows a sharp increase at the same time and then levels off.

This difference in light transmission with time and the micro-organism in the culture is distinctive and allows identification of the micro-organism within a relatively short time.

Using digital signal processing it is possible to quickly compare the growth curves found with those of one or more possible micro-organisms which could alone or in combination produce those curves.

In operation the time to normal detection of the presence of coliform micro-organisms by eye is from 2 to 14 hours. Using an optical sensor system to merely detect the colour change in the dye the time is reduced by over 30%.

The control of the temperature, the regulation of the brilliance of the light source, and the measurement of the sensor output may all be carried out by appropriately programming a CPU, with outputs being passed to an appropriate display. The output may display an indication of the number of contaminating organisms in the original sample and the type of organism. A record of the temperature and the detected light in each frequency band with time may also be recorded.

Where the environment is likely to exceed the desired temperature it is normal to use cooling to maintain the temperature constant. Since, with the knowledge of the growth curves of different micro-organisms, it is possible to predict what will happen if the temperature is not maintained constant it is an option to allow the temperature of the culture medium to vary above the desired temperature. The temperature and time are tracked, the growth curves of the organisms are tracked, and from this it is possible to predict what organisms were present initially, and in what numbers.

While a cylindrical vial is shown it is possible to use a container of a different shape, so long as it is transparent along the light path between source and sensor. In particular, because the colour change being looked for does not need to be as intense as required for detection by eye it is possible to reduce the dimensions of the vial. The lower limit for the size of the vial is determined by the minimum concentration of micro-organisms being sought. The sample size must be such that the contents are a statistical duplicate of a much larger sample.

While the invention is described in relation to water testing the invention is suitable for any material which may be dissolved, suspended or otherwise cultured in any fluid. Thus in the testing of Crustacea a shellfish may be added whole or macerated to the water with an additional growth medium and indicator for the micro-organism concerned being released by the plunger puncturing the foil seal in the cap. In the testing of milk powder the powder may be dissolved in water with added growth promotant and an indicator applied by pressing the plunger in the cap.

The apparatus itself may be readily portable and self-contained, and this together with the comparatively rapid response allows its use in situations where a normal laboratory result would too slow to be useful, as for instance in determining whether flooding has caused a pathogen problem. For use in bulk testing situations an apparatus containing multiple vials, each with a light source and detector, may be provided. The outputs are sequentially monitored by a processing and recording apparatus.

While the optical system described provides white light and is sensitive in only three colour bands it is possible to substitute a system in which a variable narrow band filter is applied to either the source or the detector, allowing a continuous scan across the ultra-violet, visible and infra-red spectrum.

Advantages of the Preferred Embodiments

Uses standard containers having multiple compartments
Standard containers have a long shelf life as the reagents are sealed in foil chambers
The containers can be used in the field without the need for skilled personnel
The containers (when used with the incubator) enable a fast test to be carried out in the field
The containers (when used with the incubator) enables the detection of very small amounts of micro-organisms (though this will take a longer time to complete the test as the micro-organisms multiply within the sample and a colour change is detected).

Variations

It is to be understood that even though numerous characteristics and advantages of the various embodiments of the present invention have been set forth in the foregoing description, together with details of the structure and functioning of various embodiments of the invention, this disclosure is illustrative only, and changes may be made in detail so long as the functioning of the invention is not adversely affected. For example the particular elements of the apparatus may vary dependent on the particular application for which it is used without variation in the spirit and scope of the present invention.

Throughout the description and claims f this specification the word "comprise" and variations of that word, such as "comprises" and "comprising", are not intended to exclude other additives, components, integers or steps.

The invention claimed is:

1. A container for testing a sample for microorganisms, comprising:
    a closable substantially rigid transparent sterile chamber configured to allow a light beam to pass into the container and be measured by one or more light detectors,
    a base and a removable cap, the cap being removable to allow insertion of a sample to be tested into the transparent chamber, and capable of then being returned to the container to seal the container, enclosing the sample within the container, and preventing the sample from escaping from the container,
    a closed second chamber and a barrier separating the second chamber from the transparent chamber, the second chamber containing a growth promoter and/or a dye adapted to assist in detecting a presence or absence of microorganisms,
    a first barrier puncturing mechanism for releasing the growth promoter and/or the dye from the second chamber into the transparent chamber without exposing the contents of the container to outside atmosphere,
    a closed third chamber and a barrier separating the third chamber from the transparent chamber, said third chamber containing a sanitizer effective to kill any microorganisms inside the container when testing is completed, and
    a second barrier puncturing mechanism for releasing the sanitizer from the third chamber into the container without exposing the contents of the container to outside atmosphere,
    wherein the closed container securely stores a liquid comprising the sample to be tested.

2. The container as claimed in claim 1, further comprising a means for locking the cap in place when the cap seals the container.

3. The container as claimed in claim 1, wherein the cap contains the second chamber and the base contains the third chamber.

4. The container as claimed in claim 3, wherein the base is of one color, and the cap is of another color to distinguish the contents of the base and the cap.

5. The container as claimed in claim 1, wherein the barrier separating the second chamber from the transparent chamber, and/or the barrier separating the third chamber from the transparent chamber, is a foil seal.

6. The container as claimed in claim 5, wherein the first and/or second barrier puncturing mechanism comprises a plunger which when depressed causes a serrated cutter to puncture the foil seal.

7. The container as claimed in claim 6, wherein the plunger is a resilient diaphragm having a convex outer surface that is recessed within the container to prevent accidental depression of the plunger.

8. A set of the containers as claimed in claim 1, wherein each container is of a same size and shape as the other containers in the set.

9. The set of containers as claimed in claim 8, wherein each container has an identical amount of the sanitizer as the other containers in the set.

10. A set of containers for testing microorganisms, each container being of a same size and shape as the other containers, each container comprising:
    a substantially rigid transparent portion configured to allow a light beam to pass into the container and be measured by one or more light detectors,
    a removable cap, the removable cap having a first compartment in the cap defined by the size of the cap and a first barrier, the first compartment containing a microorganism growth promoter and/or a dye adapted to detect the presence or absence of microorganisms,
    the cap also comprising a first barrier puncturing mechanism to enable the first barrier to be punctured to release the contents of the first compartment,
    a sanitizer compartment containing a sanitizer contained within a second barrier, and
    a second barrier puncturing mechanism for releasing the sanitizer into the container.

11. The set of containers as claimed in claim 10, wherein the transparent portion of each container is formed from UV absorbing plastics material.

12. The set of containers as claimed in claim 10, wherein the sanitizer compartment is situated in a base of the container.

13. The set of containers as claimed in claim 12, wherein the cap of each container is of a first color designating the contents of the first compartment and the base of each container is of a second color designating the contents of the sanitizer compartment.

14. The set of containers as claimed in claim 12, wherein the first and second barrier puncturing mechanism comprises a plunger, which when depressed punctures said barrier, and each plunger has a resilient convex outer surface that is recessed within the cap or base to prevent accidental depression of the plunger.

* * * * *